United States Patent
Mathissen et al.

(10) Patent No.: US 10,293,824 B2
(45) Date of Patent: May 21, 2019

(54) DUST RESUSPENSION SYSTEM FOR A MOTOR VEHICLE

(71) Applicant: FORD GLOBAL TECHNOLOGIES, LLC, Dearborn, MI (US)

(72) Inventors: Marcel Mathissen, Wurselen (DE); Volker Scheer, Roetgen (DE); Rainer Vogt, Aachen (DE)

(73) Assignee: Ford Global Technologies, LLC, Dearborn, MI (US)

( * ) Notice: Subject to any disclaimer, the term of this patent is extended or adjusted under 35 U.S.C. 154(b) by 16 days.

(21) Appl. No.: 15/372,910

(22) Filed: Dec. 8, 2016

(65) Prior Publication Data
US 2017/0166209 A1    Jun. 15, 2017

(30) Foreign Application Priority Data
Dec. 9, 2015    (DE) .................. 10 2015 224 719

(51) Int. Cl.
*B60W 10/18* (2012.01)
*G01N 15/06* (2006.01)
(Continued)

(52) U.S. Cl.
CPC ...... *B60W 30/18009* (2013.01); *B60W 10/04* (2013.01); *B60W 10/18* (2013.01);
(Continued)

(58) Field of Classification Search
CPC ........... B60W 30/18009; B60W 10/04; B60W 10/18; B60W 10/30; B60W 50/14;
(Continued)

(56) References Cited

U.S. PATENT DOCUMENTS 4,102,426 A * 7/1978 Walden .............. B60K 31/0008
                                                                180/169
5,517,298 A    5/1996 Devenport
(Continued)

FOREIGN PATENT DOCUMENTS

AT    409039 B    5/2002
CN    2052369 U    2/1990
(Continued)

OTHER PUBLICATIONS

German Search Report dated Oct. 12, 2016 for German Application No. 102015224719.8, 5 pgs.
(Continued)

*Primary Examiner* — Behrang Badii
*Assistant Examiner* — Daniel L Greene
(74) *Attorney, Agent, or Firm* — Frank A. MacKenzie; Brooks Kushman P.C.

(57) ABSTRACT

A dust resuspension system for a vehicle includes one or more dust sensors mounted to a roof, the dust sensors being configured to observe a part of a roadway surface situated ahead of the vehicle in a direction of travel and provide data of a magnitude of a road dust load of the roadway surface based on type of road surface. The system also includes a device configured to, in response to the data indicating that the magnitude of the road dust load being above a predefined threshold, implement a dust resuspension measure, wherein the measure activates a brake system to impose a forced speed restriction.

5 Claims, 1 Drawing Sheet

(51) Int. Cl.
  *B60W 50/14* (2012.01)
  *B60W 30/18* (2012.01)
  *B60W 10/04* (2006.01)
  *B60W 10/30* (2006.01)

(52) U.S. Cl.
  CPC ............ *B60W 10/30* (2013.01); *B60W 50/14* (2013.01); *G01N 15/06* (2013.01); *B60W 2420/42* (2013.01); *B60W 2550/12* (2013.01); *B60W 2550/14* (2013.01); *G01N 2015/0693* (2013.01)

(58) Field of Classification Search
  CPC ......... B60W 2420/42; B60W 2550/12; B60W 2550/14; G01N 15/06
  See application file for complete search history.

(56) References Cited

U.S. PATENT DOCUMENTS

| | | | |
|---|---|---|---|
| 6,401,520 B1 | 6/2002 | Volkwein et al. | |
| 6,592,642 B2 | 7/2003 | Maricq et al. | |
| 7,103,460 B1* | 9/2006 | Breed | B60C 23/0408 701/29.1 |
| 8,167,098 B2 | 5/2012 | Jessberger | |
| 8,497,476 B2* | 7/2013 | Hatakeyama | G01N 23/2251 250/310 |
| 2004/0255425 A1* | 12/2004 | Arai | A47L 5/28 15/300.1 |
| 2009/0224084 A1* | 9/2009 | Hoisington | A01B 79/005 239/754 |
| 2009/0265880 A1 | 10/2009 | Jessberger | |
| 2009/0300870 A1* | 12/2009 | Riach | A47L 9/1608 15/320 |
| 2011/0160920 A1* | 6/2011 | Orr | A01B 79/005 700/283 |
| 2012/0268582 A1 | 10/2012 | Rothenhausler | |
| 2013/0047703 A1 | 2/2013 | Stengel et al. | |
| 2014/0054119 A1 | 2/2014 | Hummel et al. | |
| 2014/0054120 A1 | 2/2014 | Hummel et al. | |
| 2014/0054121 A1 | 2/2014 | Hummel et al. | |
| 2014/0263720 A1* | 9/2014 | Travaglini | B05B 1/30 239/69 |
| 2015/0353291 A1* | 12/2015 | Teichrob | B65G 41/001 701/24 |
| 2016/0135655 A1* | 5/2016 | Ahn | A47L 9/2826 134/56 R |
| 2016/0280160 A1 | 9/2016 | MacNeille et al. | |

FOREIGN PATENT DOCUMENTS

| | | |
|---|---|---|
| CN | 103741629 A | 4/2014 |
| CN | 203729238 U | 7/2014 |
| CN | 204086082 U | 1/2015 |
| DE | 69009605 T2 | 9/1994 |
| DE | 10149468 A1 | 4/2003 |
| DE | 10311800 A1 | 9/2004 |
| DE | 10329961 A1 | 1/2005 |
| DE | 10329931 A1 | 2/2005 |
| DE | 202005005673 U1 | 9/2005 |
| DE | 202006004522 U1 | 6/2006 |
| DE | 202006019335 U1 | 4/2008 |
| DE | 202007000246 U1 | 5/2008 |
| DE | 102009054194 A1 | 5/2011 |
| DE | 102010002424 A1 | 9/2011 |
| DE | 102016105135 A1 | 9/2016 |
| JP | 1172327 A | 3/1991 |
| JP | 109242500 A | 9/1997 |
| JP | 2004185399 A | 7/2004 |
| JP | 20083002803 A | 12/2008 |
| KR | 100896922 B1 | 5/2009 |
| WO | 03035206 A2 | 5/2003 |

OTHER PUBLICATIONS

German Search Report dated Oct. 18, 2016 for German Application No. 102015224725.2, 6 pgs.

* cited by examiner

DUST RESUSPENSION SYSTEM FOR A MOTOR VEHICLE

CROSS-REFERENCE TO RELATED APPLICATIONS

This application claims foreign priority benefits under 35 U.S.C. § 119(a)-(d) to DE 10 2015 224 719.8 filed Dec. 9, 2015, which is hereby incorporated by reference in its entirety.

TECHNICAL FIELD

The disclosure relates to a motor vehicle having a dust sensor and to a method for reducing dust resuspension by a motor vehicle.

BACKGROUND

Traffic-related particle emissions that result not from exhaust gas but from abrasion of brakes, tires, clutches, road surface etc. and from resuspension of road dust make a considerable contribution to air pollution. It is expected that exhaust gas particle emissions will decrease owing to increasingly stringent limit values, but the other traffic-related particle emissions will increase owing to greater traffic volumes, and could become the focus of future regulations. Based on data from the German Federal Environmental Agency, it can be expected that, in the year 2020, exhaust gas particle emissions will still account for approximately 18% of all traffic-related fine dust emissions, wherein the expression "fine dust" refers to particles with aerodynamic diameters of less than 10 μm. The remaining 82% are emissions caused not by exhaust gas but by wear. This illustrates the increasing significance of particle emissions not caused by exhaust gas.

For the reduction of brake dust emissions in particular, techniques such as for example shields, blowers and dust collectors are known.

DE 10 329 961 A1 discloses a motor vehicle having an integrated fine dust extraction device for vehicles that filters and collects fine dusts out of the ambient air for scientific tests, which fine dusts can also be analyzed by way of an aerosol spectrometer as a dust measurement unit even during the collection process, wherein the measured data can be transmitted by radio.

Also, motor vehicles have already been proposed by means of which it is sought to remove fine dusts from the ambient air during travel.

For example, DE 20 2006 019 335 U1 discloses a fine-dust extraction device for vehicles, by means of which fine dusts can be removed from the fresh air supplied to the vehicle interior compartment, but by means of which it is also possible for the fine dust content in the ambient air to be reduced in order to comply with legally prescribed fine dust limit values.

DE 20 2006 004 522 U1 discloses a fine dust filter that operates with electrical or magnetic separation and is arranged between an air inlet grille and radiators of a vehicle for the purposes of removing fine dusts from the ambient air flowing through there, even fine dusts that have been emitted or resuspended by other vehicles.

DE 20 2005 005 673 U1 discloses an outside-air filter for motor vehicles, which outside-air filter is mounted below a bumper and serves for the general reduction of air pollution.

Such systems would be capable of effectively reducing fine dust in the environment only if they were installed in a very large number of vehicles, and the outlay for cleaning the numerous filters and for the disposal of the collected dusts would be extreme, especially as relatively coarse dusts that are not actually harmful would also be collected, and the filters would quickly become full.

DE 10 2009 054 194 A discloses a vehicle having a head-up display and having a camera introduced into the beam path thereof, and, from the image data of the camera, it is also possible for rain or dirt on the windshield to be detected.

JP H09 242 500 A discloses an environmental measurement vehicle having a dust concentration sensor arranged on the roof.

SUMMARY

The disclosure is based on the object of making it possible to preventatively reduce dust resuspension by motor vehicles and, if appropriate, implement targeted countermeasures.

According to the disclosure, the dust sensor is a sensor for observing a part of a roadway surface situated ahead of the vehicle in a direction of travel. A sensor of said type makes it possible to obtain images of the roadway surface in an arbitrary range of the electromagnetic spectrum, such as for example visible or invisible light or radar waves. On the basis of said images or similar observation data relating to the roadway surface obtained by sensor means, automatic estimation of the magnitude of the road dust load of that part of the roadway surface that is situated ahead of the vehicle is performed in the motor vehicle in real time.

The disclosure makes it possible, on roadway sections that are identified as being generally laden with dust, to targetedly counteract a resuspension or re-release of fine dust, for example through temporary influencing of the vehicle speed and/or by way of targeted but temporary air cleaning measures.

According to a study of road states in central Europe, the greatest part of the particle emissions not caused by exhaust gas arises with a particularly high level of introduction of dirt only on 10% of the road network.

The disclosure therefore makes it possible for the restrictions and the outlay associated with reducing resuspension or re-release of fine dust to be kept within limits because said measures can be restricted to particularly contaminated roadway sections. With this relatively low outlay, it is possible to realize a relatively great environmental benefit.

Although most human drivers will also seek to not cause excessive dust resuspension when driving, it is normally the case that, when they identify dust resuspension or the potential for it, it is too late to react. Modern image evaluation methods can estimate the road dust load of the roadway section situated ahead of the vehicle earlier and more reliably than human drivers, specifically in good time before a situation conducive to dust resuspension arises.

The sensor may be a camera and/or a laser scanner and/or a part of a radar system. Forward-facing cameras, laser scanners and radars are image-recording systems that are often installed as standard, or that can at least be ordered as options, in modern motor vehicles. The image-recording systems may either obtain two-dimensional images or scan the roadway surface line by line.

In the case of a camera as a sensor, which may also be a stereo camera, the dust load of a road or the potential for the road dust load thereof may be estimated, for example, on the basis of deviations in certain image features, such as color changes, brightness etc. An indication for possible dust load is the composition of the road surface, for example asphalted, non-asphalted, concrete, gravel, etc. The composition of the road surface may be determined in accordance with its typical appearance, and use may also be made of pattern recognition methods and the like.

If the road surface is observed by being scanned using a laser scanner or radar, a measurement point cloud or a height profile is obtained in which road parts suspected of having a dust load can be found, for example damage to the road surface or rail crossings, at which relatively high dust emissions are typically detected.

Height profile data and optical camera data may also be amalgamated in order to make the estimation more accurate.

The estimated values provided by the device for estimating the road dust load may be filtered in order that only the most heavily dust-laden roadway sections, which are thus most susceptible to dust resuspension, are taken into consideration.

The road dust load of the roadway surface may be specified as a particle concentration, which is correlated with the dust emissions to be expected.

The data obtained may be used as input parameters for a device for reducing dust resuspension. Said device may involve the following:

- a water-based dust reduction system, which sprays water onto the roadway and/or the tires of the vehicle but only if high dust emissions are to be expected, such that the water reservoir required for this purpose does not have to be very large;
- an electrostatically operating dust reduction system that is active only when high dust emissions are to be expected such that the container required for separated-off dust does not have to be very large;
- a dust reduction system based on conventional filter media, in particular felts, nonwovens, synthetic fibers, fabric filters or similar media, in the case of which the air flow is conducted via the filter only if high dust emissions are to be expected, such that the filter service life is considerably lengthened;
- a human-machine interface that asks or prompts the driver to reduce speed in order to avoid high dust emissions because these increase over-proportionately with driving speed. A prompt to reduce speed may, for example, be provided in the form of known optical displays for economic driving, with green representing low dust emissions, yellow representing medium dust emissions and red representing high dust emissions;
- a forced speed restriction of the vehicle if high dust emissions owing to misuse are to be expected, for example in the event of driving at excessive speed with spiked tires; and
- a cloud server of a vehicle ad hoc network for vehicle-to-vehicle communication to which the data obtained, together with geolocation data of the vehicle, can be uploaded and which, from the collected data from a very large number of vehicles, creates a dust load map that represents a real-time map of the potential for dust load. The mass data obtained in this way can be made available to the owners of road infrastructure, or to those responsible for the road infrastructure, who can then implement suitable countermeasures, for example can set local speed restrictions for all vehicles or only for vehicles without a dust reduction system, and/or can arrange to have affected road sections cleaned more frequently.

Exemplary embodiments will be described below on the basis of the drawings. In the drawings:

DETAILED DESCRIPTION

As required, detailed embodiments of the present disclosure are disclosed herein; however, it is to be understood that the disclosed embodiments are merely exemplary of the disclosure that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure.

Figure 1:
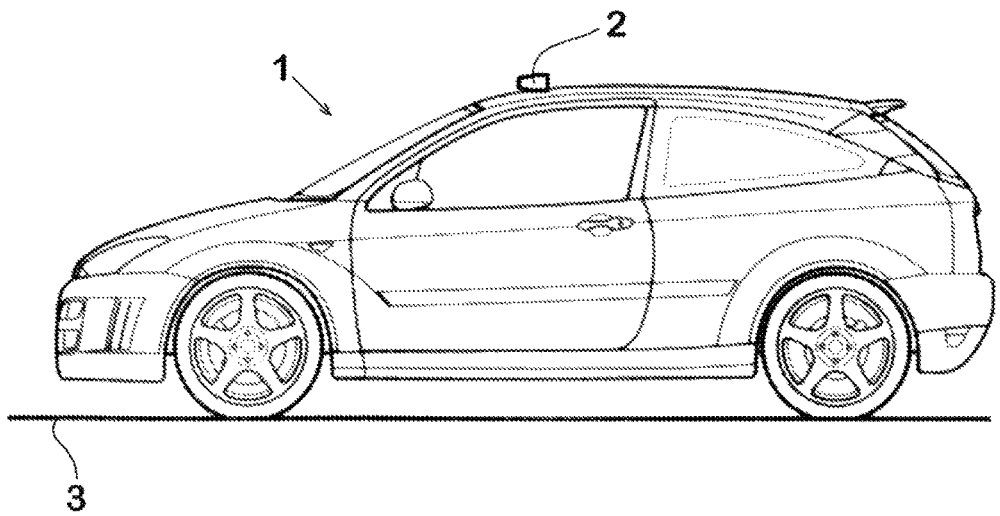
FIG. 1 shows a schematic side view of a motor vehicle with a dust sensor.

The motor vehicle 1 shown in FIG. 1 has a sensor 2 mounted at the highest possible point for the purposes of observing a part of a roadway surface 3 situated ahead of the vehicle in a direction of travel. The sensor 2 is schematically shown as being situated on top of the roof of the motor vehicle, but could for example also be installed behind the windshield, in side mirrors or at some other suitable location. Sensor 2 may comprise one camera, and it is also possible for stereo cameras, a laser scanner, a radar sensor or an array of such sensors to be used, which are arranged at suitable locations in or on the motor vehicle.

The sensor 2 may be a camera and/or a laser scanner and/or a part of a radar system. Forward-facing cameras, laser scanners and radars are image-recording systems that are often installed as standard, or that can at least be ordered as options, in modern motor vehicles. The image-recording systems may either obtain two-dimensional images or scan the roadway surface line by line.

Figure 2:
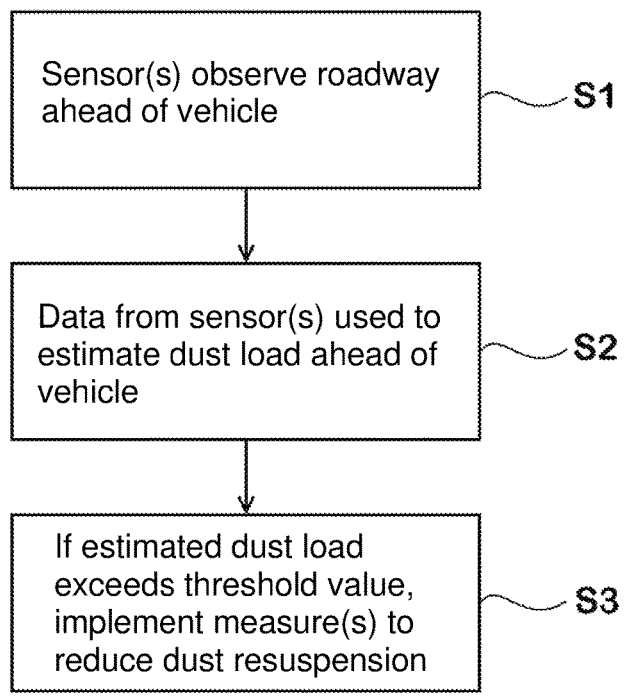
FIG. 2 shows a flow diagram of a method for reducing dust resuspension by a motor vehicle.

Referring to FIG. 2, during driving operation of the motor vehicle 1, that part of the roadway surface, which is situated ahead of the vehicle, is observed by sensor(s) 2, which may be performed optically or by way of radar or other optical or radar-based sensors (step S1). On the basis of the observation data, the road dust load in the observed part of the roadway surface is estimated (step S2). If, and only if, the estimated value for the road dust load in the observed part of the roadway surface exceeds a threshold value, measures for reducing dust resuspension are implemented (step S3), for example binding dust or filtering out dust and/or working toward a reduction of the driving speed of the vehicle.

In the case where the sensor 2 is a camera, which may also be a stereo camera, the dust load of a road or the potential for the road dust load thereof may be estimated, for example, on the basis of deviations in certain image features, such as color changes, brightness etc. An indication for possible dust load is the composition of the road surface, for example asphalted, non-asphalted, concrete, gravel, etc. The composition of the road surface may be determined in accordance with its typical appearance, and use may also be made of pattern recognition methods and the like.

A measure for reducing dust resuspension may be achieved by operating a human-machine interface that asks or prompts the driver to reduce speed in order to avoid high dust emissions because these increase over-proportionately with driving speed. A prompt to reduce speed may, for example, be provided in the form of known optical displays for economic driving, with green representing low dust emissions, yellow representing medium dust emissions and red representing high dust emissions;

Another measure for reducing dust resuspension may be a forced speed restriction of the vehicle if high dust emissions owing to misuse are to be expected, for example in the event of driving at excessive speed with spiked tires If the sensor 2 comprises a laser scanner or radar operative to scan the road surface, a measurement point cloud or a height profile may be obtained in which road parts suspected of having a dust load can be found, for example damage to the road surface or rail crossings, at which relatively high dust emissions are typically detected.

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure. Additionally, the features of various implementing embodiments may be combined to form further embodiments of the disclosure.

What is claimed is:

1. A method for reducing dust resuspension by a motor vehicle comprising:

operating a dust sensor on the vehicle to observe a part of a roadway surface ahead of the motor vehicle in a direction of travel; and responsive to an estimate of road dust load present at the part of the roadway surface derived from data from the dust sensor, prompting a driver of the vehicle to reduce a driving speed of the motor vehicle.

2. The method as claimed in claim 1 further comprising, implementing at least one further measures for reducing dust resuspension in addition to the prompting of the driver to reduce the driving speed of the motor vehicle.

3. The method as claimed in claim 1, wherein the dust sensors comprises an array of laser scanners that detect a height profile of the roadway surface, and the estimate is based at least in part upon damage to the road surface indicated by the height profile of the roadway surface.

4. The method as claimed in claim 1, wherein the dust sensor is operative to obtain an image of the road surface ahead of the vehicle, determines a composition of the road surface base at least in part on the image, and the estimate of the dust load is based at least in part upon the composition of the road surface.

5. The method as claimed in claim 4, wherein the dust sensors comprises a stereo camera.

* * * * *